United States Patent
Whitsett et al.

(10) Patent No.: US 9,404,927 B2
(45) Date of Patent: Aug. 2, 2016

(54) SYSTEMS AND METHODS FOR DIAGNOSING AND TREATING CANCER

(71) Applicant: The Translational Genomics Research Institute, Phoenix, AZ (US)

(72) Inventors: Timothy G. Whitsett, Phoenix, AZ (US); Nhan L. Tran, Phoenix, AZ (US)

(73) Assignee: The Translational Genomics Research Institute, Phoenix, AZ (US)

(*) Notice: Subject to any disclaimer, the term of this patent is extended or adjusted under 35 U.S.C. 154(b) by 0 days.

(21) Appl. No.: 14/561,313

(22) Filed: Dec. 5, 2014

(65) Prior Publication Data

US 2015/0323538 A1  Nov. 12, 2015

Related U.S. Application Data

(60) Provisional application No. 61/912,067, filed on Dec. 5, 2013.

(51) Int. Cl.
| | |
|---|---|
| *C07H 21/02* | (2006.01) |
| *C07H 21/04* | (2006.01) |
| *A61K 48/00* | (2006.01) |
| *G01N 33/574* | (2006.01) |
| *C12Q 1/68* | (2006.01) |
| *A61K 31/713* | (2006.01) |
| *A61K 45/06* | (2006.01) |
| *C12N 15/113* | (2010.01) |

(52) U.S. Cl.
CPC ........ *G01N 33/57423* (2013.01); *A61K 31/713* (2013.01); *A61K 45/06* (2013.01); *C12N 15/1138* (2013.01); *C12Q 1/6886* (2013.01); *C12N 2310/11* (2013.01); *C12N 2310/14* (2013.01); *C12N 2320/30* (2013.01); *C12Q 2600/158* (2013.01)

(58) Field of Classification Search
CPC ... C12N 2310/11; C12N 15/111; A61K 48/00
See application file for complete search history.

(56) References Cited

U.S. PATENT DOCUMENTS

2010/0215588 A1* 8/2010 Skaliter ................ C12N 15/111
424/45

\* cited by examiner

*Primary Examiner* — Amy Bowman

(57) ABSTRACT

Embodiments of the invention provide a method detecting and treating cancer, such as lung cancer. In some aspects, the method may include detecting cancer in a subject, which may comprise assessing the expression of a marker in a sample from the subject. For example, the marker may comprise c-Met and/or Fn14. In some embodiments, if the subject is diagnosed as having cancer, the method may further provide administering a therapeutically effective amount of a substance that reduces the expression level of Fn14 to the subject to reduce the invasive and migratory capabilities of the cancer.

2 Claims, 6 Drawing Sheets

| NSCLC Specimens | Antigen 1 | Antigen 2 | p value |
|---|---|---|---|
| Adenocarcinoma | Fn14 | c-Met | 0.00002 |
| Squamous Cell | Fn14 | c-Met | 0.01 |

FIG. 1B  Correlation between Fn14 and c-Met by Kendall's Tau

| Patient | Type | Primary NSCLC | | Patient-Matched Metastasis | |
|---|---|---|---|---|---|
| | | c-Met IHC | Fn14 IHC | c-Met IHC | Fn14 IHC |
| 1 | S | 1 | 1 | 3 | 2 |
| 2 | A | 1 | 3 | 3 | 3 |
| 3 | A | 1 | 2 | 3 | 2 |
| 4 | S | 3 | 2 | 2 | 2 |
| 5 | A | 0 | 3 | NA | 3 |
| 6 | A | 3 | 2 | 3 | 3 |
| 7 | A | 3 | 3 | 3 | 3 |
| 8 | A | 0 | 1 | 3 | 3 |
| 9 | A | 1 | 2 | 2 | 1 |
| 10 | A | 1 | 1 | 3 | 3 |
| 11 | A | 2 | 2 | 2 | 2 |
| 12 | S | 0 | 1 | 2 | 3 |
| 13 | S | 1 | 1 | 0 | 1 |
| 14 | A | 3 | 3 | 2 | 2 |
| IHC Score 2/3 | | 36% | 64% | 92% | 86% |

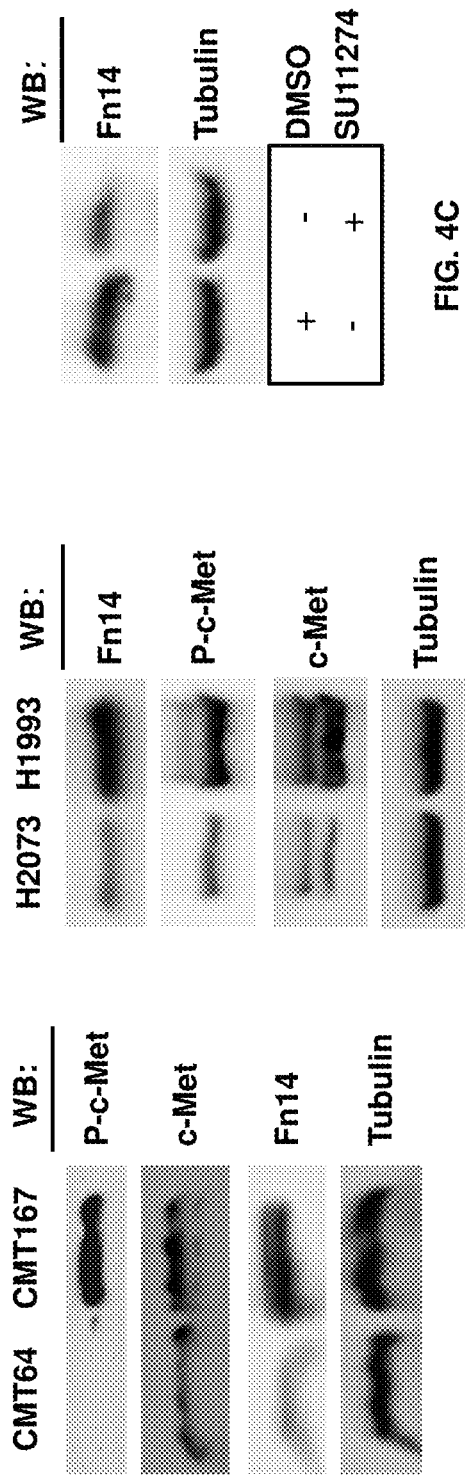

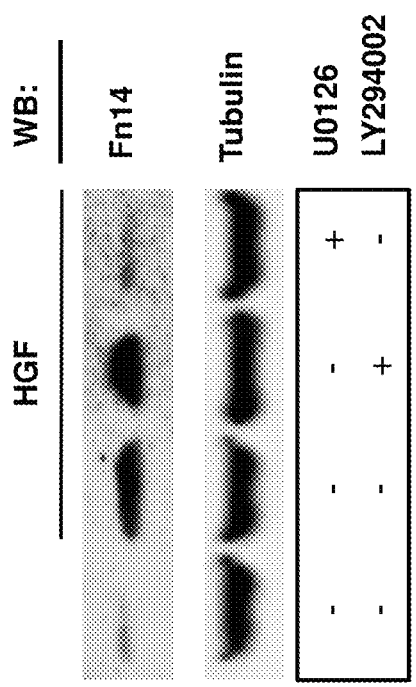
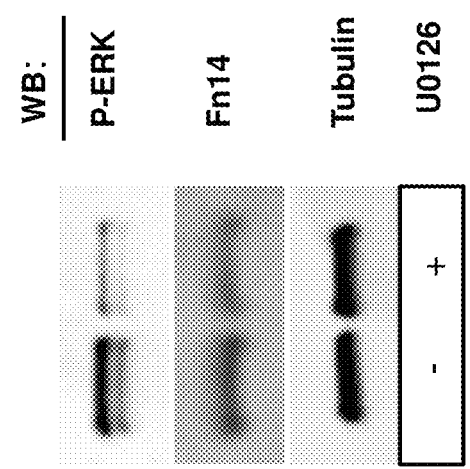
FIG. 5A
FIG. 5B

SYSTEMS AND METHODS FOR DIAGNOSING AND TREATING CANCER

CROSS-REFERENCE TO RELATED APPLICATIONS

The present application claims priority to U.S. Patent Application No. 61/912,067 filed Dec. 5, 2013, which is hereby incorporated by reference in its entirety.

STATEMENT REGARDING FEDERALLY SPONSORED RESEARCH

This invention was made with government support under CA130940 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 24 kilobyte ASCII (text) file named "cMet_Fn14_ST25" created Dec. 2, 2014.

FIELD OF THE INVENTION

The present invention is generally related to systems and methods for diagnosing and treating one or more forms of cancer, and particularly related to systems and methods for diagnosing and treating non-small cell lung cancer.

BACKGROUND OF THE INVENTION

Lung cancer remains the leading cause of cancer mortality in the US and throughout the world (Jemal A, et al. (2011) Global cancer statistics. CA Cancer J Clin 61 2): 69-90), with most patients presenting with advanced stage disease. The five-year survival rate for advanced stage non-small cell lung cancer (NSCLC) remains below 10%, necessitating the need for novel therapeutic strategies against advanced disease (Heist R S, Engelman J A (2012) SnapShot: non-small cell lung cancer. Cancer Cell 21 3): 448 e2). A significant clinical hurdle to reduce mortality in NSCLC is the propensity for tumor cell invasiveness and metastasis. Despite pharmacological advances for NSCLC, current treatments have limited efficacy in metastatic disease, and the majority of patients succumb to the overwhelming tumor burden resulting from tumor spread. Even molecularly targeted therapeutics such as the epidermal growth factor receptor-tyrosine kinase inhibitors (EGFR-TKIs) fail due to tumor resistance, followed by disease progression. Two targets associated with NSCLC metastasis are the hepatocyte growth factor receptor (HGFR/c-Met) and fibroblast growth factor-inducible 14 (Fn14).

c-Met and its cognate ligand, hepatocyte growth factor (HGF), have been associated with tumor progression and metastasis in many solid tumor types (Stella G M, Benvenuti S, Comoglio P M (2010) Targeting the MET oncogene in cancer and metastases. Expert Opin Investig Drugs 19 11): 1381-94). Within adenocarcinomas, the most common subtype of NSCLC, the protein expression of c-Met was detected in ~30% of cases and c-Met gene amplification was seen in 10% of cases (Tsuta K, et al. (2012) c-MET/phospho-MET protein expression and MET gene copy number in non-small cell lung carcinomas. J Thorac Oncol 7 2): 331-9). Increased c-Met activity has been observed to occur secondary to oncogenic activation of k-Ras (Yang Y, et al. (2008) A selective small molecule inhibitor of c-Met, PHA-665752, reverses lung premalignancy induced by mutant K-ras. Mol Cancer Ther 7 4): 952-60), while gene amplification of c-Met is often a mechanism of resistance to EGFR-TKIs (Bean J, et al. (2007) MET amplification occurs with or without T790M mutations in EGFR mutant lung tumors with acquired resistance to gefitinib or erlotinib. Proc Natl Acad Sci USA 104 52): 20932-7).

Furthermore, the expression of c-Met was more common in poorly differentiated adenocarcinomas compared to well-differentiated tumors (Tsuta K, et al. (2012) c-MET/phospho-MET protein expression and MET gene copy number in non-small cell lung carcinomas. J Thorac Oncol 7 2): 331-9). Among all types of NSCLC, c-Met expression was also significantly correlated with brain metastasis (Benedettini E, et al. (2010) Met activation in non-small cell lung cancer is associated with de novo resistance to EGFR inhibitors and the development of brain metastasis. Am J Pathol 177 1): 415-23). Ectopic expression of both HGF and c-Met in the NSCLC cell line H460 induced spontaneous metastasis to distant organs (Navab R, et al. (2009) Co-overexpression of Met and hepatocyte growth factor promotes systemic metastasis in NCI-H460 non-small cell lung carcinoma cells. Neoplasia 11 12): 1292-300). Thus, an improved understanding of HGF/c-Met signaling may offer novel therapeutic opportunities against advanced metastatic NSCLC.

The TNF-like weak inducer of apoptosis (TWEAK)-Fn14 signaling axis has been implicated in tumor growth, cell survival, and tumor invasion. Increased expression of Fn14 has been observed in a number of solid tumors, including hepatocellular carcinoma (Feng S L, et al. (2000) The Fn14 immediate-early response gene is induced during liver regeneration and highly expressed in both human and murine hepatocellular carcinomas. Am J Pathol 156 4): 1253-61), glioblastoma (GB) (Tran N L, et al. (2003) The human Fn14 receptor gene is up-regulated in migrating glioma cells in vitro and overexpressed in advanced glial tumors. Am J Pathol 162 4): 1313-21; Tran N L, et al. (2006) Increased fibroblast growth factor-inducible 14 expression levels promote glioma cell invasion via Rac1 and nuclear factor-kappaB and correlate with poor patient outcome. Cancer Res 66 19): 9535-42), esophageal adenocarcinoma (Watts G S, et al. (2007) Identification of Fn14/TWEAK receptor as a potential therapeutic target in esophageal adenocarcinoma. Int J Cancer 121 10): 2132-9), and HER2+ breast cancer (Willis A L, et al. (2008) The fibroblast growth factor-inducible 14 receptor is highly expressed in HER2-positive breast tumors and regulates breast cancer cell invasive capacity. Mol Cancer Res 6 5): 725-34). Fn14 is also highly expressed in NSCLC (Whitsett T G, et al. (2012) Elevated expression of Fn14 in non-small cell lung cancer correlates with activated EGFR and promotes tumor cell migration and invasion. Am J Pathol 181 1): 111-20), and Fn14 expression significantly correlates with activated EGFR. Additionally, Fn14 expression was maintained at a high level in NSCLC cells resistant to EGFR-TKIs. In GB, Fn14 signaling modulated cell survival through regulation of NF-κB, Bcl-xL, and Bcl-2 expression and Akt2 activation (Fortin S P, et al. (2009) Tumor necrosis factor-like weak inducer of apoptosis stimulation of glioma cell survival is dependent on Akt2 function. Mol Cancer Res 7 11): 1871-81; Tran N L, et al. (2005) The tumor necrosis factor-like weak inducer of apoptosis (TWEAK)-fibroblast growth factor-inducible 14 (Fn14) signaling system regulates glioma cell survival via NFkappaB pathway activation and BCL-XL/BCL-W expression. J Biol Chem 280 5): 3483-92). Fn14 signaling also promoted glioma and breast cell invasion through activation of Rac1 and NF-κB (Tran N L, et al. (2006) Increased fibroblast growth factor-inducible 14 expression levels promote glioma cell invasion via Rac1 and nuclear factor-kappaB and correlate with poor patient outcome. Cancer Res 66 19): 9535-42; Willis A L, et al. (2008) The fibroblast growth factor-inducible 14 receptor is highly expressed in HER2-positive breast tumors and regulates breast cancer cell invasive capacity. Mol Cancer Res 6 5): 725-34).

In NSCLC, Fn14 signals to induce cell migration and invasion in vitro, and ectopic expression of Fn14 enhanced metastasis in vivo (Whitsett T G, et al. (2012) Elevated expression of Fn14 in non-small cell lung cancer correlates with activated EGFR and promotes tumor cell migration and invasion. Am J Pathol 181 1): 111-20). Thus, Fn14 may play a critical role in cancer cell invasion and metastasis and represent a potential therapeutic vulnerability in advanced stage NSCLC. Efforts to directly target the TWEAK/Fn14 signaling pathway are currently under investigation (Zhou H, et al. (2011) Development and characterization of a potent immunoconjugate targeting the Fn14 receptor on solid tumor cells. Mol Cancer Ther 10 7): 1276-88), and clinical trials are ongoing (http://clinicaltrials.gov/ct2/show/NCT01383733).

In view of the aforementioned, there is a need to further understand Fn14 and c-Met expression and whether these markers are correlated in NSCLC tumors (e.g., primary tumors) and/or metastatic lesions. There is also a need to understand c-Met signaling and if c-Met signaling enhances Fn14 protein expression. Moreover, there is further a need to understand the potential impact of depletion of Fn14 on c-Met driven cell migration and invasion to understand the overall role of c-Met and Fn14 in an invasive phenotype of NSCLC.

SUMMARY OF THE INVENTION

Some embodiments of the invention provide a method of diagnosing cancer that can comprise receiving a sample from a subject suspected of having cancer and detecting a level of expression of at least one growth factor receptor and Fn14 in the sample from the subject. In some aspects, the levels of expression of the at least one growth factor receptor and Fn14 are determined relative to a control sample. As such, in some aspects, the subject can be diagnosed as having cancer when the levels of expression of the at least one growth factor receptor and Fn14 are both elevated compared to the control sample. In some aspects, the type of cancer may be a form of lung cancer, such as non-small cell lung cancer. Moreover, the one or more growth factors may be selected from the list consisting of c-Met, EGFR, FGFR, VEGFR, and IGFR. Further, in some aspects, if the subject is diagnosed as having cancer, the method may include administering a therapeutically effective amount of a pharmaceutical composition to the subject. In some embodiments, the pharmaceutical composition may comprise an inhibitor of the at least one growth factor and/or Fn14.

Some embodiments of the invention may also provide a method of detecting and treating cancer (e.g., a cancer, such as lung cancer), which may include initially detecting a cancer in a subject. The steps may include receiving a sample from the subject suspected of having cancer, adding a first reagent capable of binding to at least one growth factor receptor (e.g., c-Met, EGFR, FGFR, VEGFR, IGFR) to a mixture comprising the sample, and adding a second reagent capable of binding to Fn14 to the mixture comprising the sample. Thereafter, the method may include subjecting the mixture to conditions that allow detection of the binding of the first and second reagents and then diagnosing the subject as having cancer when the levels of expression of the at least one growth factor receptor and Fn14 are both elevated compared to a control sample. In addition, the method may then include administering to the subject a therapeutically effective amount of a pharmaceutical composition that inhibits Fn14 or the at least one growth factor when the in the subject is diagnosed as having cancer. For example, the pharmaceutical composition may inhibit the expression of Fn14 through the inclusion of small RNAs that target SEQ ID NO: 3. Moreover, in some aspects, the pharmaceutical composition may reduce the capacity of the cancer to metastasize to other tissues from its primary location.

Some embodiments of the invention provide a method of predicting a metastatic potential of a tumor in a subject that has been diagnosed with cancer. For example the method may include receiving a sample from a subject that has been diagnosed with cancer, detecting a level of expression of c-Met in the sample from the subject and also detecting a level of expression of Fn14 in the sample from the subject. In some aspects, the levels of expression of c-Met and Fn14 are determined relative to the expression of c-Met and Fn14 in a control sample. In some embodiments, the level of expression of c-Met and Fn14 are correlated with the metastatic potential of the cancer. For example, in some aspects, greater expression levels of c-Met and Fn14 can be correlated with a greater likelihood that the cancer will metastasize to other locations in the subject. In some embodiments, the cancer may be a form of lung cancer, such as non-small cell lung cancer. Additional objectives, advantages and novel features will be set forth in the description which follows or will become apparent to those skilled in the art upon examination of the drawings and detailed description which follows.

Additional objectives, advantages and novel features will be set forth in the description which follows or will become apparent to those skilled in the art upon examination of the drawings and detailed description which follows.

BRIEF DESCRIPTION OF THE DRAWINGS

FIGS. 1A-1D illustrate the FN14 expression in patient NSCLC tumors correlates with c-Met. (FIG. 1A) Fn14 and c-Met staining on representative samples from one patient (5× objective, Aperio GL Scanner). (FIG. 1B) Tumor-cell specific Fn14 and c-Met staining in each of the tumor punches was scored by a board-certified pathologist; a score of zero indicates staining level equal to adjacent non-tumor cells. A non-zero score indicates increased staining (1=minimum, 2=moderate, 3=strong positive). A total of 290 samples were scored for Fn14 and c-Met expression and the correlation between the two stains was analyzed using Kendall's tau rank correlation test, adjusted for multiple testing. The mRNA expressions of Fn14 and c-Met were examined in (FIG. 1C) lung adenocarcinomas (AC) and (FIG. 1D) squamous cell lung carcinomas (SCC) using publically available gene expression data (www.genesapiens.org). Statistical correlations are performed on the website.

(FIG. 2A) IHC scoring of Fn14 and c-Met in patient-matched primary and metastatic lung tumors. (FIG. 2B) Combined Fn14 and c-Met IHC scores were compared by Student's t test. * represents a p value <0.05.

FIGS. 4A-4C illustrate that c-Met amplification enhances Fn14 expression levels in NSCLC cell lines. (FIG. 4A) Total cell lysates were prepared from CMT64 and CMT167 cell lines and immunoblotted with the indicated antibodies. Tubulin was used as a loading control. (FIG. 4B) Total cell lysates were prepared from H2073 (primary adenocarcinoma NSCLC cell line) and H1993 (patient-matched metastatic cell line with known c-Met amplification) and immunoblotted with the indicated antibodies. Tubulin was used as a loading control. (FIG. 4C) H1993 cells were treated with vehicle or SU11274 for 24 hr. Cells were harvested, total cell lysates were prepared and immunoblotted with an antibody against Fn14. Tubulin was used as a loading control.

FIGS. 5A and 5B illustrate that inhibition of MEK or ERK abrogates HGF-induced expression of Fn14. (FIG. 5A) Serum starved H2073 cells pre-treated with either vehicle, U0126, or LY294002 for 30 minutes were exposed to HGF (20 ng) for three hours. Cells were harvested, total cell lysates were prepared and immunoblotted with antibodies to Fn14. Tubulin was used as a loading control. (FIG. 5B) H1993 cells were treated with either vehicle or U0126 for three hours Immunoblots for phosphorylated ERK1/2 (pERK1/2) and Fn14 were performed with tubulin used as a loading control.

(FIG. 6A) H1993 cells were infected with lentiviruses expressing Fn14 shRNA or control non-targeting shRNA. Stable cell lines were isolated, cell lysates prepared, and immunoblotting was conducted using the indicated antibodies to Fn14 or tubulin (loading control). (FIG. 6B) Transwell migration assay of H1993 cell lines expressing control shRNA or Fn14 shRNA. (FIG. 6C) Matrigel invasion assay of H1993 cell lines expressing control shRNA or Fn14 shRNA. For migration and invasion assays, the values shown are mean±SEM of triplicate chambers, and all experiments were duplicated. * represents a p value <0.05, and was considered statistically significant by Student's t test.

Figure 1C:
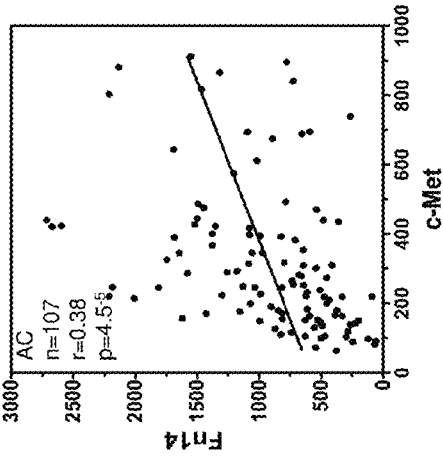

The headings used in the figures should not be interpreted to limit the scope of the claims.

DETAILED DESCRIPTION

Some embodiments of the invention provide methods of detecting, diagnosing, and/or treating a disease, such as cancer. Moreover, some embodiments of the invention provide methods of assessing the progress of the disease and/or predicting patient outcome/decline. For example, some embodiments of the invention include methods of diagnosing cancer and/or treating the cancer. In some aspects, the cancer may comprise lung cancer, which may further include non-small cell lung cancer. Some embodiments of the invention may also include determining the relative stage of a lesion (e.g., a metastatic lesion) that is associated with the cancer. Some embodiments comprise the use of detecting, quantifying, and/or augmenting the presence of one or more markers. In some embodiments of the invention, the marker may comprise one or more growth factor receptors (e.g., c-Met, EGFR, FGFR, VEGFR, IGFRs, etc.) and/or Fn14. In particular, some embodiments include augmenting (e.g., increasing or decreasing) a level of expression of the one or more markers and then providing a therapeutic modality to a patient to treat the cancer.

Generally, some embodiments of the present invention can be used to identify, quantify, detect, assess, isolate, and/or augment expression levels of one or more markers. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alliteratively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frame shift mutations, single nucleotide polymorphisms (SNPs), inversions, translocations, heterochromatic insertions, and differentially methylated sequences relative to a reference gene, whether alone or in combination.

In some embodiments of the invention, the marker may comprise a plurality of markers. For example, the plurality of markers may include one or more molecules that are known to bind to growth factors, such as growth factor receptors. In some aspects, the growth factor receptors may include any known growth factor receptors now known or discovered in the future. In some aspects, the growth factor receptors may be c-Met, epidermal growth factor receptor (EGFR), any fibroblast growth factor receptor (FGFR), vascular endothelial growth factor (VEGFR), insulin-like growth factor receptor (IGFR), etc. Moreover, in some aspects, one or more of the markers may comprise Fn14. In some aspects, a combination of one or more of the above-described potential markers can be looked at in combination with other markers to provide diagnostic, prognostic, and/or therapeutic information for one skilled in the art in the context of one or more cancers (e.g., NSCLC). In some particular aspects, the combination of the markers may include an analysis of c-Met mRNA (SEQ ID NO: 1) or protein (SEQ ID NO: 2) expression in combination with Fn14 mRNA (SEQ ID NO: 3) or protein (SEQ ID NO: 4) expression.

An allele of a gene may or may not produce a functional protein; may produce a protein with altered function, localization, stability, dimerization, or protein-protein interaction; may have overexpression, under-expression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Q3 replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications. For example, as described in greater detail herein, in some aspects of the invention, a first reagent can be used to detect c-Met and a second reagent can be used to detect Fn14. In some embodiments, the first and/or the second reagents may comprise one or more oligonucleotides (e.g., primers) that can specifically bind to DNA, RNA, and/or cDNA to detect the presence and/or expression of nucleic acids that correspond to c-Met (SEQ ID NO: 1) and/or Fn14 (SEQ ID NO: 3) using techniques such as PCR, qPCR, qRT-PCR, northern blot, etc.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent), stain, enzyme, or nonradioactive metal. Specific examples include, but are not limited to: fluorescein, biotin, digoxigenin, alkaline phosphates, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphthalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "marker" specificity. Marker sequences are "markers" in the sense that they are sought to be sorted out from other nucleic acid. Amplification techniques have been designed primarily for this sorting out.

The term "template" refers to nucleic acid originating from a sample that is analyzed for the presence of a marker of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays. For example, as described in greater detail herein, in some aspects of the invention, a first reagent can be used to detect c-Met and a second reagent can be used to detect Fn14. In some embodiments, the first and/or the second reagents may comprise one or more oligonucleotides (e.g., primers) that can specifically bind to DNA, RNA, and/or cDNA to detect the presence and/or expression of nucleic acids that correspond to c-Met (SEQ ID NO: 1) and/or Fn14 (SEQ ID NO: 3) using techniques such as PCR, qPCR, qRT-PCR, northern blot, etc.

Some embodiments of the invention may include assessing, determining, quantifying, or altering the expression of a marker. As used herein expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Other examples include any process of assessing expression that uses an antibody including the following nonlimiting examples, flow cytometry, immunohistochemistry, ELISA, Western blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a marker. Such methods also include direct methods used to assess protein expression including the following nonlimiting examples: HPLC, mass spectrometry, protein microarray analysis, PAGE analysis, isoelectric focusing, 2-D gel electrophoresis, and enzymatic assays. For example, as described in greater detail herein, in some aspects of the invention, a first reagent can be used to detect c-Met and a second reagent can be used to detect Fn14. In some embodiments, the first and/or the second reagents may comprise one or more antibodies that can specifically bind to protein to detect the presence and/or expression of proteins that correspond to c-Met (SEQ ID NO: 2) and/or Fn14 (SEQ ID NO: 4). For example, the first and second reagents in the protein context can be assessed using techniques such as immunohistochemistry, western blot analysis, flow cytometry, ELISA, and immunoaffinity chromatography. Samples from which expression may be detected include single cells, whole organs or any fraction of a whole organ, whether in vitro, ex vivo, in vivo, or post-mortem.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or nonfluorescent), stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RTPCR measured in $\Delta Ct$ or alternatively in the number of PCR cycles necessary to reach a particular optical density at a wavelength at which a double stranded DNA binding dye (e.g. SYBR Green) incorporates, through release of label from a previously labeled reporter probe used in a real-time RTPCR reaction, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a marker in existence now or yet to be developed. In some aspects of the invention, positive expression is a sufficient level of expression to correlate with a particular response such as susceptibility to cancer recurrence.

In some aspects of the invention, reduced expression constitutes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1 \times 10^{-5}$ greater or less expression normalized to the expression of a housekeeping gene.

The invention contemplates assessing the expression of the marker(s) in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. In one aspect of the invention, the sample comprises primary or metastatic NSCLC cells. In another, the sample comprises sputum. In another aspect of the invention, the sample comprises blood or other tissues obtained from a subject who has been diagnosed with or is suspected of having NSCLC.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

In some aspects of the invention, the cancer cells are derived from NSCLC, which comprises any carcinoma derived from lung tissues that does not include small cell lung cancers. Examples of non-small cell lung cancers include adenocarcinomas, large cell carcinomas, and squamous cell carcinomas of the lung.

The pathologic stages of non-small cell lung cancer include, but are not limited to the following: in the occult or hidden stage, cancer cells may be found in sputum, but no tumor can be found in the lung by bronchoscopy or other imaging. In Stage 0, also called carcinoma in situ, abnormal cells are found in the innermost lining of the lung. Such abnormal cells are precancerous and may or may not become malignant and spread into nearby tissue.

In Stage I, a cancer has developed. There are two substages to stage 1. In Stage IA, the tumor presents only in the lung only and is 3 centimeters or smaller. For the disease to be considered stage 1B, it will have one or more of the following traits: the tumor is larger than 3 centimeters, the cancer has spread to the main bronchus of the lung, and is at least 2 centimeters from the carina, the cancer has spread to the innermost layer of the membrane that covers the lungs, or the tumor partly blocks the bronchus or bronchioles and part of the lung has collapsed or developed pneumonitis (inflammation of the lung).

Similarly, there are two substages to Stage II. In Stage IIA, the tumor is 3 centimeters or smaller and cancer has spread to nearby lymph nodes on the same side of the chest as the tumor. For the disease to be considered, Stage IIB, the cancer has spread to nearby lymph nodes on the same side of the chest as the tumor and it will have one or more of the following traits: the tumor is larger than 3 centimeters, the cancer has spread to the main bronchus of the lung and is 2 centimeters or more from the carina, the cancer has spread to the innermost layer of the membrane that covers the lungs, or the tumor partly blocks the bronchus or bronchioles and part of the lung has collapsed or developed pneumonitis (inflammation of the lung). Alternatively, the disease may be classified as Stage 2B if the cancer has not spread to the lymph nodes and it displays one or more of the following traits: cancer has spread to the chest wall, or the diaphragm, or the pleura between the lungs, or membranes surrounding the heart, the cancer has spread to the main bronchus of the lung and is no more than 2 centimeters from the carina, but has not spread to the trachea, cancer blocks the bronchus or bronchioles and the whole lung has collapsed or developed pneumonitis (inflammation of the lung). Stage III is also divided into two substages.

In stage IIIA, cancer has spread to lymph nodes on the same side of the chest as the tumor and it displays one or more of the following traits: cancer has spread to the main bronchus, the chest wall, the diaphragm, the pleura around the lungs, or the membrane around the heart, but has not spread to the trachea, or part or all of the lung may have collapsed or developed pneumonitis (inflammation of the lung). In stage IIIB, the tumor has spread to one or more of the following: lymph nodes above the collarbone or in the opposite side of the chest from the tumor, to the heart, to major blood vessels that lead to or from the heart, to the chest wall, to the diaphragm, to the trachea, to the esophagus, to the sternum or spine, to more than one area in the same lobe of the lung, or to the fluid of the pleural cavity surrounding the lung.

In stage IV, cancer may have spread to lymph nodes and has spread to another lobe of the lung or to other parts of the body, such as the brain, liver, adrenal glands, kidneys, or bone.

The present invention further provides kits to be used in assessing the expression of a marker in a subject to assess the risk of developing disease, diagnosing the subject as having a stage of the disease, or determining to which stage the disease has progressed. Kits include any combination of components that facilitates the performance of an assay. A kit that facilitates assessing the expression of the markers may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate hybridization, as previously described.

In some aspects of the invention, a probe may be affixed to a solid substrate. In other aspects of the invention, the sample may be affixed to a solid substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate in the case of a Southern Blot.

Some embodiments of the invention may include the administration of a pharmaceutical composition or a pharmacological composition to a subject that has been diagnosed with cancer. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The concept of a pharmaceutical composition encompasses a compound or a pharmaceutically acceptable salt thereof with or without any other additive. The physical form of the invention may affect the route of administration and one skilled in the art would know to choose a route of administration that takes into consideration both the physical form of the compound and the disorder to be treated. Pharmaceutical compositions may be prepared using methodology well known in the pharmaceutical art.

In some aspects of the invention, the pharmaceutical composition can comprise one or more compounds or products that are capable of treating a subject with NSCLC. In some embodiments, the pharmaceutical composition may comprise or include one or more compounds that are capable of affecting the markers. The pharmaceutical composition may comprise one or more compounds that are capable of augmenting the expression of one or more of the markers. For example, the pharmaceutical composition may comprise one or more compounds that are capable of reducing expression of one or more of the markers. In some aspects, the one or more compounds can reduce the transcription, translation, and/or post-translational processes associated generally or specifically with one or more of the markers.

For example, in some embodiments, the pharmaceutical composition may comprise one or more compounds that are capable of inhibiting the expression and/or function of one or more growth factor receptors and/or Fn14. In these aspects, the one or more compounds may comprise siRNA, shRNA, antibodies, or other molecules that are capable of inhibiting the expression and/or function of the one or more growth factor receptors and/or Fn14. As used herein, "inhibit" or "inhibiting" may refer to a complete or partial reduction in expression (translational, transcriptional, post-translational, etc.) or a complete or partial reduction in function of one or more of the markers.

By way of example only, in some embodiments, the markers may comprise c-Met and/or Fn14 and the one or more compounds in one or more pharmaceutical compositions may be capable of affecting c-Met and/or Fn14. In some aspects, the c-Met inhibitors may comprise compounds, small molecules, antibodies, etc. including but not limited to tivantinib, PF04217903, AMG337, EMD12144063, INCB028060, onartuzumab, ficlatuzumab, rilotumumab, TAK701, crizotinib, cabozantinib, foretinib, E7050, ANG707, MGCD265, etc. Moreover, in some aspects, Fn14 inhibitors may include siRNA, shRNA, antibodies, or other molecules are now known or may be discovered in the future, such as those disclosed in U.S. patent application Ser. No. 14/327,448, which is hereby incorporated by reference for any purposes. In some aspects, the one or more compounds, siRNA, shRNA, antibodies, or other molecules may be capable of affecting the growth factors and/or Fn14 via the augmentation of the ligands for these molecules (e.g., EGF, VGF, Insulin, HGF, TWEAK, etc.). For example, the pharmaceutical composition may comprise an compound that inhibits binding of the ligand to the target (e.g., c-Met or Fn14) or the pharmaceutical composition may comprise a compound, such as an antibody that binds to a ligand and depletes the ligand from the local or systemic environment.

A pharmaceutical composition may include a second effective compound of a distinct chemical formula from the disclosed compound. This second effective compound may have the same or a similar molecular target as the marker or it may act upstream or downstream of the molecular target of the compound with regard to one or more biochemical pathways. Moreover, in some aspects, the second pharmaceutical composition can be other chemotherapeutic compounds, such as a platinum-derived pharmaceutical (e.g., cisplatin, carboplatin, etc.), paclitaxel, pemetrexed, bevacizumab, etc. In addition, the second pharmaceutical composition can comprise other therapies, such as radiation.

In addition, in some aspects, one or more treatments can be provided in the event of the detection of one or more of the markers. By way of example only, in some aspects, detection of increased expression of one or more of the markers (e.g., c-Met and/or Fn14) can be indicative of a negative prognosis (e.g., indicative of the fact that the cancer is likely to metastasize). In these situations, some embodiments of the invention comprise the administration of one or more prophylactic treatments (e.g., radiation) to reduce the likelihood of metastasis and/or reduce the impact of the metastases (e.g., prophylactic cranial irradiation).

Pharmaceutical compositions include materials capable of modifying the physical form of a dosage unit. In one nonlimiting example, the composition includes a material that forms a coating that contains the compound. Materials that may be used in a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or multi-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions may also include at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. Compounds may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension. Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Determination of an effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

Treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of a compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions may be administered prior to, concurrently with, or after administration of additional or second pharmaceutical compositions. Concurrent administration means compositions are administered within about one minute of each other. If not administered concurrently, the additional or second pharmaceutical compositions may be administered a period of one or more minutes, hours, days, weeks, or months before or after the pharmaceutical composition that includes the currently disclosed compound. Alliteratively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of one or more active ingredients. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

Overall, some embodiments of the invention include systems and methods for the diagnosis of a condition, assessing the prognosis of the condition, and treating the condition. Particular embodiments comprise the use of one or more markers (e.g., c-Met and/or Fn14) to diagnosis one or more forms of cancer and/or assessing the likely stage of progression of the cancer. For example, the one or more markers can be used to diagnose and/or assess the likely stage of the cancer. In some aspects, the cancer may comprise non-small cell lung cancer. Moreover, some embodiments of the invention may further provide treating a cancer, such as non-small cell lung cancer. For example, the method of treatment may comprise altering the expression of one or more markers (e.g., c-Met-induced Fn14 expression), which can result in an abrogation of tumor migration and invasion of some forms of cancer.

EXAMPLES

Materials and Methods

Tumor Tissue Microarray

The construction and use of tissue microarrays (TMA) from primary patient NSCLC tumor specimens has been previously described (Whitsett T G, et al. (2012) Elevated expression of Fn14 in non-small cell lung cancer correlates with activated EGFR and promotes tumor cell migration and invasion. Am J Pathol 181 1): 111-20). Immunohistochemistry (IHC) analysis for Fn14 was done using the Fn14 monoclonal antibody P4A8 (Biogen Idec, Inc.) as previously described (Tran N L, et al. (2006) Increased fibroblast growth factor-inducible 14 expression levels promote glioma cell invasion via Rac1 and nuclear factor-kappaB and correlate with poor patient outcome. Cancer Res 66 19): 9535-42; Whitsett T G, et al. (2012) Elevated expression of Fn14 in non-small cell lung cancer correlates with activated EGFR and promotes tumor cell migration and invasion. Am J Pathol 181 1): 111-20). c-Met analysis was performed using an antibody specific for c-Met (kindly provided by Dr. George Vande Woude, Van Andel Research Institute). A scoring system for each chromophore comprised of staining intensity and extensiveness captured the outcome: 0, negative; 1, weak; 2 moderate; 3, strong. Tests for correlation using the rank based Kendall's tau statistic were calculated using the cor.test function in the R statistical package. P-values were adjusted for multiple testing and a p<0.05 was considered significant.

Metastatic Lung Cancer Mouse Model $KRas^{G12D}/LKB1^{lox/lox}$ were generated by selective breeding of Lox-Stop-Lox $KRas^{G12D}$ mice (Jackson E L, et al. (2001) Analysis of lung tumor initiation and progression using conditional expression of oncogenic K-ras. Genes Dev 15 24): 3243-8) purchased from Jackson Laboratories (Bar-Harbor, Me.) with $LKB1^{lox/lox}$ mice obtained from Mouse Repository at the NCI and described previously (Bardeesy N, et al. (2002) Loss of the Lkb1 tumour suppressor provokes intestinal polyposis but resistance to transformation. Nature 419 6903): 162-7), and were inbred on a FVB background. Induction of lung tumors was performed as described previously (DuPage M, Dooley A L, Jacks T (2009) Conditional mouse lung cancer models using adenoviral or lentiviral delivery of Cre recombinase. Nat Protoc 4 7): 1064-72). Briefly, six-week-old $KRas^{G12D}/LKB1^{lox/lox}$ mice were transiently infected with $5\times10^6$ p.f.u. of Cre adenovirus (University of Iowa adenoviral core) via intranasal infection. $KRas^{G12D}/LKB1^{lox/lox}$ mice were monitored post-infection for clinical signs of disease (labored breathing, severe weight loss), at which time mice were euthanized, necropsied and grossly evaluated for metastases. Primary and suspected metastatic lung tumors were collected and prepared for immunohistological analysis using routine procedures. Following confirmation of status of metastatic lesion, matching primary and metastatic tumors were sectioned and stained for Fn14 (#ab109365) and c-Met (#ab101539) using antibodies purchased from Abcam (Cambridge, Mass.) using previously described procedures (Whitsett T G, et al. (2012) Elevated expression of Fn14 in non-small cell lung cancer correlates with activated EGFR and promotes tumor cell migration and invasion. Am J Pathol 181 1): 111-20).

Cell Culture

Human NSCLC cell lines H2073 and H1993 (American Type Culture Collection, Manassas, Va.) and mouse cell lines CMT64 and CMT167 (Sigma-Aldrich, St. Louis, Mo.) were maintained in RPMI 1640 (Invitrogen, Carlsbad, Calif.) and DMEM (Invitrogen), respectively, supplemented with 10% heat-inactivated fetal bovine serum (FBS) in a 37° C., 5% $CO_2$ atmosphere. For the HGF stimulation, cells were placed in RPMI 1640 without FBS for 18 hours prior to growth factor exposure.

Reagents, Antibodies and Immunoblot Analysis

HGF was purchased from Millipore (Billerica, Mass.). SU11274 and U0126 were purchased from Selleck Chemicals (Houston, Tex.). LY294002 was purchased from Tocris Biosciences (R&D Systems, Minneapolis, Minn.). The final concentrations of inhibitors were SU11274 (2 µM), U0126 (10 µM), and LY294002 (10 µM). Antibodies for immunblot analysis against Fn14, c-Met, and phosphorylated c-Met were purchased from Cell Signaling Technology (Danvers, Mass.), while alpha-tubulin was purchased from Millipore. Immunoblot analysis was performed as previously described (Whitsett T G, et al. (2012) Elevated expression of Fn14 in non-small cell lung cancer correlates with activated EGFR and promotes tumor cell migration and invasion. Am J Pathol 181 1): 111-20).

Lentiviral Constructs and Transduction

Lentiviral constructs (pGIPZ) containing non-silencing shRNA or shRNA targeting the Fn14 transcript (Fn14shRNA156, clone ID V3LHS_380156) were purchased from Open Biosystems (Huntsville, Ala.). A non-silencing shRNAmir vector was used as a control in knockdown experiments. VSV-G pseudo-typed recombinant lentiviruses encoding Fn14 were produced by co-transfection of 293 packaging cells with the pCDH-Fn14 HA construct and the pPACK packaging mix (System Biosciences) according to the manufacturer's directions. Pseudo-typed lentiviruses encoding shRNAs were produced by co-transfection of packaging cells with the appropriate shRNA construct and the Trans-lentiviral packaging extract (Open Biosystems) according to the manufacturer's protocol. For lentiviral transduction, medium containing recombinant lentiviruses was harvested from the packaging cells at 48 hours post-transfection, concentrated by PEG precipitation and centrifugation, and added to sub-confluent cultures of cells together with 8 µg/ml polybrene.

Migration and Invasion

Migration was assessed using a 25×80 mm polycarbonate membrane (8 µM pore) and 12-well Chemotaxis Chamber (Neuro Probe Inc., Gaithersburg, Md.). Cells ($5\times10^4$) were seeded into each of 12 wells and allowed to migrate through the membrane for 5 hr. Cells were maintained in RPMI 1640 (Invitrogen) without FBS throughout the experiment. All treatments were performed in triplicate. Stationary cells were removed from the top of the membrane by scraping and the membrane was fixed in 70% methanol. The membrane was stained with DAPI and mounted on a glass slide. Cells were counted from 5 random fields using fluorescent microscopy. A p value ≤0.05 was considered statistically significant as determined using the two sample Student's t-test. For the invasion assays, cells ($1\times10^5$) suspended in RPMI 1640 with 0.5% serum were seeded into growth factor-reduced Matrigel invasion chambers (BD Biosciences). Chambers were placed in a 24-well plate containing RPMI 1640 and 10% FBS. Cells were allowed to invade through the membrane for 20 hr. All treatments were performed in triplicate. Cells were fixed and stained with DAPI. Stationary cells were removed from the top of the membrane by scraping and the membrane was mounted on a glass slide. Cells were counted from five random fields using light microscopy. Statistical analyses were done as described for the migration assays.

Results

Figure 1D:
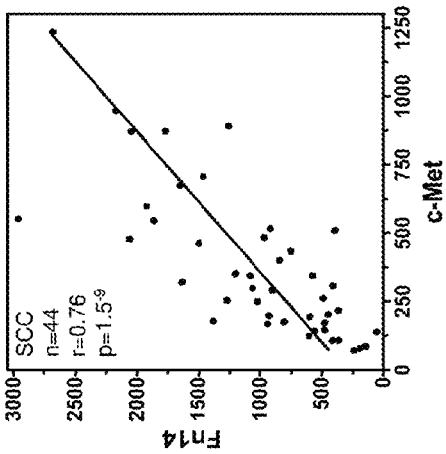
Figure 1A:
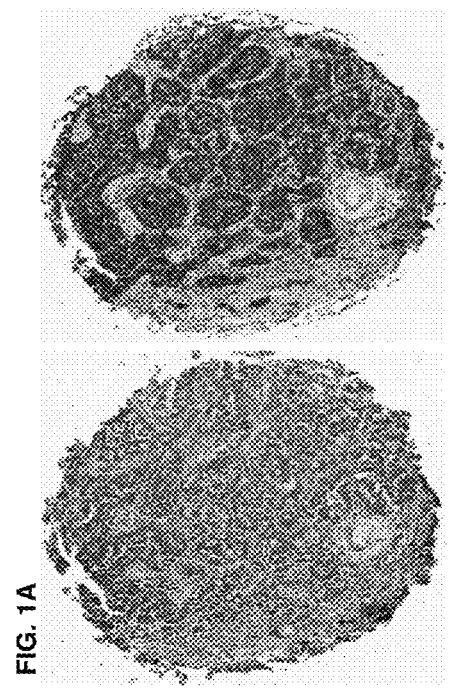

Fn14 is Over-Expressed in Primary Human NSCLC Tumors and Correlates with c-Met Levels Elevated expression of c-Met has been observed in metastatic lesions compared to primary lung tumors (Benedettini E, et al. (2010) Met activation in non-small cell lung cancer is associated with de novo resistance to EGFR inhibitors and the development of brain metastasis. Am J Pathol 177 1): 415-23). Thus, we examined a NSCLC tissue microarray by IHC to determine whether those tumors with elevated Fn14 also expressed c-Met. Representative staining patterns of an Fn14 positive/c-Met positive patient are shown in FIG. 1A. To determine whether Fn14 protein (SEQ ID NO: 4) correlated with c-Met protein (SEQ ID NO: 2) expression, tumors were scored for both Fn14 and c-Met staining intensity. There was a statistically significant positive correlation (p value <0.01)

between Fn14 and c-Met expression in both adenocarcinoma and squamous cell carcinoma subtypes as determined by the Kendall's tau rank correlation test (FIG. 1B). In addition, significant positive correlation was observed between the mRNA expression levels of Fn14 and c-Met in both lung adenocarcinomas (FIG. C) and squamous cell lung carcinoma (FIG. 1D) samples in a publically available dataset.

Fn14 and c-Met are Highly Expressed in Lung Cancer Metastases

Figures 2A, 2B:
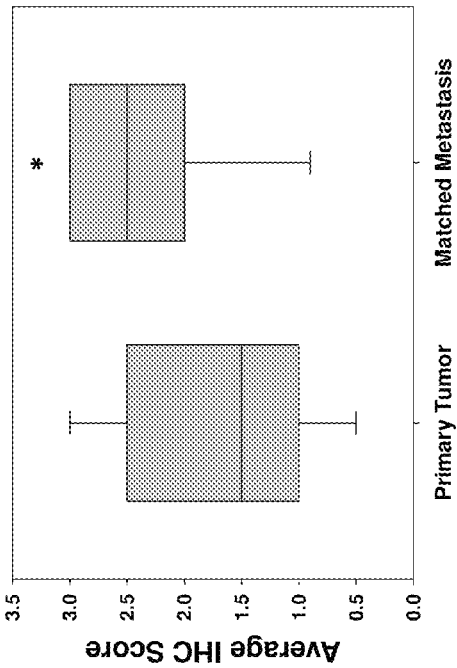
FIGS. 2A and 2B illustrate that Fn14 and c-Met expressions are elevated in metastatic lesions compared to patient-match primary tumors.

Next, we examined by IHC staining of human primary lung tumors and their matched metastases whether Fn14 and c-Met were expressed. In fourteen cases of matched primary lung and metastatic tumors from NSCLC patients, Fn14 and c-Met were more highly expressed in the metastatic tumors (FIG. 2A). In the metastatic tumor samples, 12/13 displayed elevated (IHC score of 2-3) c-Met protein expression, and 12/14 displayed elevated Fn14 protein expression. The combined, averaged IHC score for both Fn14 and c-Met were significantly elevated in the metastatic tumors relative to their matched primary lung tumors (FIG. 2B).

Figure 3:
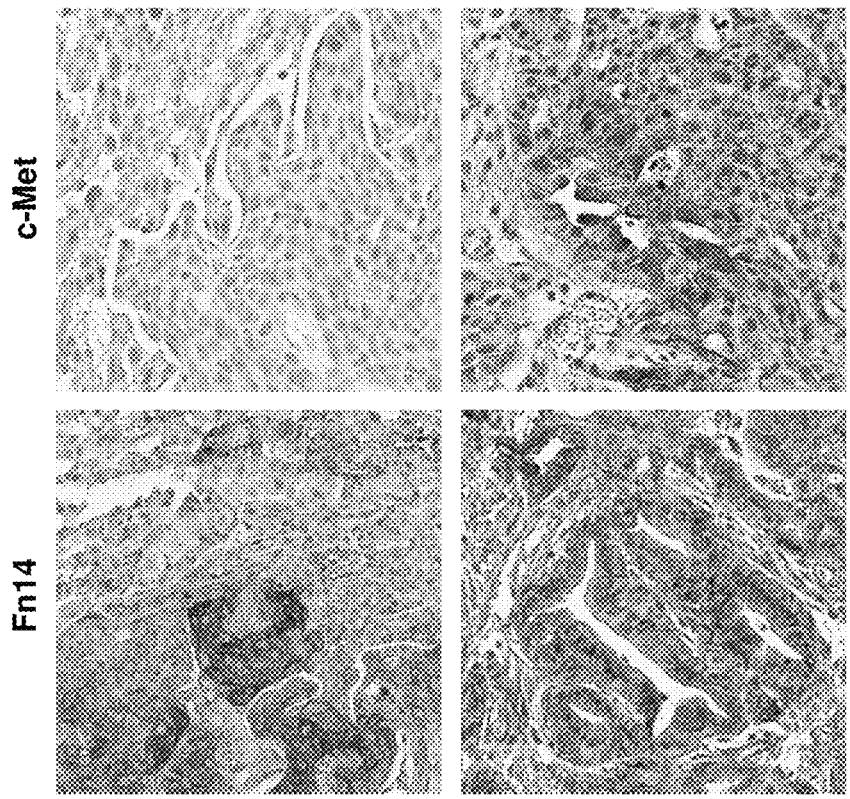
FIG. 3 illustrates that metastatic NSCLC lesions express both Fn14 and c-Met in a transgenic model of NSCLC. Images of matched primary and metastatic NSCLC tumors present in KRas$^{G12D}$/LKB1$^{lox/lox}$ mice stained for Fn14 and c-Met. Representative images were taken with a 20× objective.

Using an in vivo mouse model of metastatic lung cancer, we further investigated the protein expression of Fn14 and c-Met. Transient expression of Cre and subsequent expression of KRas$^{G12D}$ and homozygous deletion of LKB1 within the lungs of the KRas$^{G12D/LKB}$1$^{lox/lox}$ mice results in multifocal, highly aggressive NSCLC with both local and distant metastases (Ji H, et al. (2007) LKB1 modulates lung cancer differentiation and metastasis. Nature 448 7155): 807-10; Chen Z, et al. (2012) A murine lung cancer co-clinical trial identifies genetic modifiers of therapeutic response. Nature 483 7391): 613-7). Consistent with these previous findings, we found that KRas$^{G12D}$/LKB1$^{lox/lox}$ mice with significant signs of clinical disease (labored breathing, severe weight loss) 8-10 weeks post-infection with Cre adenovirus harbored distant metastases to several sites (data not shown). Following histological confirmation of metastatic NSCLC at these distant sites, we stained for Fn14 and c-Met protein expression in matched primary and metastatic NSCLC tumors from these mice. Although both the primary and matched NSCLC tumors displayed Fn14 staining, intensity of Fn14 staining within the primary tumor appeared more heterogeneous, whereas staining intensity of Fn14 within metastatic NSCLC lesions appeared more uniform (FIG. 3). Interestingly, primary NSCLC lesions from KRas$^{G12D/LKB}$1$^{lox/lox}$ mice displayed low or no staining of c-Met (FIG. 3), while the matched metastatic lesions displayed increased c-Met staining (FIG. 3).

Fn14 is Highly Expressed in c-Met-Driven NSCLC Cell Lines

We next investigated the relationship between Fn14 and c-Met in a mouse cell line model of matched primary and metastatic tumors. The CMT64 cell line was established from a spontaneous lung carcinoma in a mouse (Franks L M, et al. (1976) Metastasizing tumors from serum-supplemented and serum-free cell lines from a C57BL mouse lung tumor. Cancer Res 36 3): 1049-55), while the CMT167 is a highly metastatic subline of CMT64 (Layton M G, Franks L M (1984) Heterogeneity in a spontaneous mouse lung carcinoma: selection and characterisation of stable metastatic variants. Br J Cancer 49 4): 415-21). We examined the protein levels of phosphorylated and total c-Met, Fn14 and tubulin in these cell lines. The metastatic CMT167 cells displayed elevated protein levels of both total and activated c-Met with concomitant elevated protein expression of Fn14 compared to CMT64 cells (FIG. 4A).

To further confirm the elevated protein expression of c-Met and Fn14 in metastatic tumors, we examined an in vitro model of patient-matched primary lung cancer and lymph node metastasis. The H2073 and H1993 cells lines represent a primary lung adenocarcinoma and lymph node metastasis derived from the same patient; respectively, and H1993 has been reported to harbor c-Met receptor amplification (Benedettini E, et al. (2010) Met activation in non-small cell lung cancer is associated with de novo resistance to EGFR inhibitors and the development of brain metastasis. Am J Pathol 177 1): 415-23). H1993 showed elevated total and activated c-Met protein as previously described. In conjunction, H1993 displayed elevated Fn14 protein expression compared to H2073 (FIG. 4B). We next investigated whether the elevated expression of Fn14 in H1993 was dependent on c-Met signaling. H1993 cells treated with the c-Met inhibitor, SU11274, showed inhibition of the Fn14 protein expression (FIG. 4C).

c-Met-Induced Fn14 is MAPK Dependent

The HGF activation of c-Met is known to induce downstream signaling activity through both the MAPK and PI3K pathways (Gherardi E, et al. (2012) Targeting MET in cancer: rationale and progress. Nat Rev Cancer 12 2): 89-103). We sought to determine whether HGF-induced Fn14 expression was dependent upon MAPK and/or PI3K signaling. In H2073 cells, exposure to HGF enhanced protein expression of Fn14 (FIG. 5A). Pretreatment of the cells with U0126 (a MEK inhibitor) completely abrogated the HGF-induced Fn14 expression, whereas LY294002 (PI3K inhibitor) had no effect on HGF-induced Fn14 expression (FIG. 5A). In the lymph node-derived H1993 cells, where both c-Met and Fn14 proteins are elevated, exposure of the cells to U0126 significantly decreased Fn14 protein expression (FIG. 5A).

Fn14 Depletion Reduces NSCLC Cell Migration and Invasive Capacity In Vitro

Figure 6C:
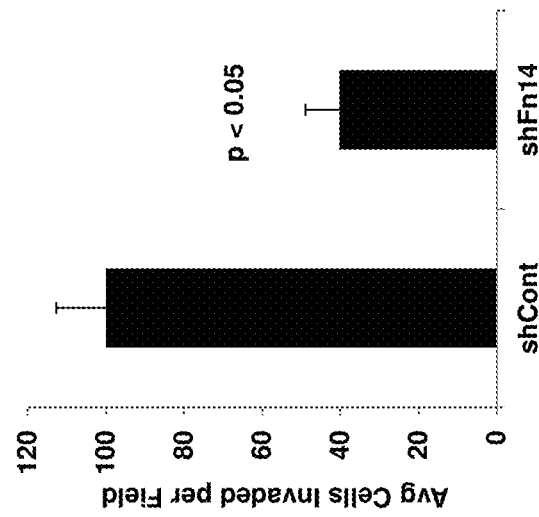
FIGS. 6A-6C illustrate that depletion of Fn14 expression by shRNA reduces NSCLC cell migration and invasion.
Figure 6B:
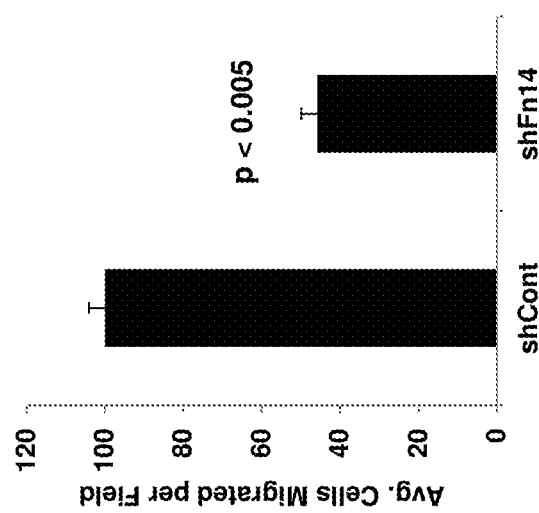
Figure 6A:
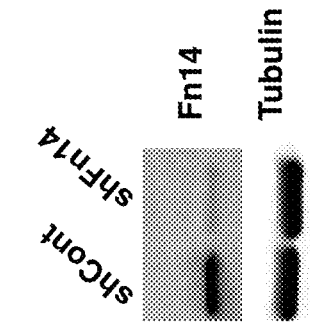

We next investigated whether depletion of Fn14 expression by shRNA could suppress c-Met-driven NSCLC cell migration and invasion. H1993 (metastasis derived) cells are highly motile compared to H2073 (primary tumor derived) cells (Benedettini E, et al. (2010) Met activation in non-small cell lung cancer is associated with de novo resistance to EGFR inhibitors and the development of brain metastasis. Am J Pathol 177 1): 415-23). H1993 cells stably expressing shRNA targeting the Fn14 transcript showed ~90-95% decreased Fn14 (FIG. 6A), and were found to be significantly less migratory and invasive in comparison to empty vector (sh-Cont) containing cells. Specifically, the knockdown of Fn14 by shRNA significantly suppressed H1993 cell migration by 60% (FIG. 6B) and cell invasion through Matrigel by 55% (FIG. 6C). The reduction observed with Fn14 depletion is similar to that observed between H1993 and patient-matched H2073 cells (Benedettini E, et al. (2010) Met activation in non-small cell lung cancer is associated with de novo resistance to EGFR inhibitors and the development of brain metastasis. Am J Pathol 177 1): 415-23).

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of diagnosing non-small cell lung cancer, the method comprising the steps of:
   receiving a sample from a subject suspected of having non-small cell lung cancer;
   detecting a level of expression of c-Met in the sample from the subject, wherein the level of expression of c-Met is determined relative to a control sample;
   detecting a level of expression of Fn14 in the sample from the subject, wherein the level of expression of Fn14 is determined relative to the control sample; and
   wherein the subject is diagnosed as having cancer when the levels of expression of the at least one growth factor receptor and Fn14 are both elevated compared to the control sample.

2. The method of claim 1, further comprising treating the non-small cell lung cancer once the subject has been diagnosed, the method of treating the non-small cell lung cancer comprising administering a therapeutically effective amount of a pharmaceutical composition to the subject, wherein the pharmaceutical composition comprises at least one of an inhibitor of Fn14 and c-Met.

* * * * *

SEQUENCE LISTING

<160> NUMBER OF SEQ ID NOS: 4

<210> SEQ ID NO 1
<211> LENGTH: 6641
<212> TYPE: DNA
<213> ORGANISM: Homo sapiens

<400> SEQUENCE: 1

| | | | | | |
|---|---|---|---|---|---|
| gccctcgccg | cccgcggcgc | cccgagcgct | ttgtgagcag | atgcggagcc | gagtggaggg | 60 |
| cgcgagccag | atgcggggcg | acagctgact | tgctgagagg | aggcggggag | gcgcggagcg | 120 |
| cgcgtgtggt | ccttgcgccg | ctgacttctc | cactggttcc | tgggcaccga | aagataaacc | 180 |
| tctcataatg | aaggccccg | ctgtgcttgc | acctggcatc | ctcgtgctcc | tgtttacctt | 240 |
| ggtgcagagg | agcaatgggg | agtgtaaaga | ggcactagca | aagtccgaga | tgaatgtgaa | 300 |
| tatgaagtat | cagcttccca | acttcaccgc | ggaaacaccc | atccagaatg | tcattctaca | 360 |
| tgagcatcac | attttccttg | gtgccactaa | ctacatttat | gttttaaatg | aggaagacct | 420 |
| tcagaaggtt | gctgagtaca | agactgggcc | tgtgctggaa | cacccagatt | gtttcccatg | 480 |
| tcaggactgc | agcagcaaag | ccaatttatc | aggaggtgtt | tggaaagata | acatcaacat | 540 |
| ggctctagtt | gtcgacacct | actatgatga | tcaactcatt | agctgtggca | gcgtcaacag | 600 |
| agggacctgc | cagcgacatg | tctttcccca | caatcatact | gctgacatac | agtcggaggt | 660 |
| tcactgcata | ttctccccac | agatagaaga | gcccagccag | tgtcctgact | gtgtggtgag | 720 |
| cgccctggga | gccaaagtcc | tttcatctgt | aaaggaccgg | ttcatcaact | tctttgtagg | 780 |
| caataccata | aattcttctt | atttcccaga | tcatccattg | cattcgatat | cagtgagaag | 840 |
| gctaaaggaa | acgaaagatg | gttttatgtt | tttgacggac | cagtcctaca | ttgatgtttt | 900 |
| acctgagttc | agagattctt | accccattaa | gtatgtccat | gcctttgaaa | gcaacaattt | 960 |
| tatttacttc | ttgacggtcc | aaagggaaac | tctagatgct | cagacttttc | acacaagaat | 1020 |
| aatcaggttc | tgttccataa | actctggatt | gcattcctac | atggaaatgc | ctctggagtg | 1080 |
| tattctcaca | gaaagagaa | aaagagatc | cacaaagaag | gaagtgttta | atatacttca | 1140 |
| ggctgcgtat | gtcagcaagc | ctgggggccca | gcttgctaga | caaataggag | ccagcctgaa | 1200 |
| tgatgacatt | cttttcgggg | tgttcgcaca | aagcaagcca | gattctgccg | aaccaatgga | 1260 |
| tcgatctgcc | atgtgtgcat | tccctatcaa | atatgtcaac | gacttcttca | acaagatcgt | 1320 |
| caacaaaaac | aatgtgagat | gtctccagca | ttttttacgga | cccaatcatg | agcactgctt | 1380 |
| taataggaca | cttctgagaa | attcatcagg | ctgtgaagcg | cgccgtgatg | aatatcgaac | 1440 |
| agagtttacc | acagctttgc | agcgcgttga | cttattcatg | ggtcaattca | gcgaagtcct | 1500 |
| cttaacatct | atatccacct | tcattaaagg | agacctcacc | atagctaatc | ttgggacatc | 1560 |
| agagggtcgc | ttcatgcagg | ttgtggtttc | tcgatcagga | ccatcaaccc | ctcatgtgaa | 1620 |
| ttttctcctg | gactccatc | cagtgtctcc | agaagtgatt | gtggagcata | cattaaacca | 1680 |
| aaatggctac | acactggtta | tcactgggaa | gaagatcacg | aagatcccat | tgaatggctt | 1740 |
| gggctgcaga | catttccagt | cctgcagtca | atgcctctct | gccccaccct | ttgttcagtg | 1800 |
| tggctggtgc | cacgacaaat | gtgtgcgatc | ggaggaatgc | ctgagcggga | catggactca | 1860 |
| acagatctgt | ctgcctgcaa | tctacaaggt | ttttcccaaat | agtgcacccc | ttgaaggagg | 1920 |
| gacaaggctg | accatatgtg | gctgggactt | tggatttcgg | aggaataata | aatttgattt | 1980 |
| aaagaaaact | agagttctcc | ttggaaatga | gagctgcacc | ttgactttaa | gtgagagcac | 2040 |
| gatgaataca | ttgaaatgca | cagttggtcc | tgccatgaat | aagcatttca | atatgtccat | 2100 |

```
aattatttca aatggccacg ggacaacaca atacagtaca ttctcctatg tggatcctgt    2160
aataacaagt atttcgccga aatacggtcc tatggctggt ggcactttac ttactttaac    2220
tggaaattac ctaaacagtg ggaattctag acacatttca attggtggaa aaacatgtac    2280
tttaaaaagt gtgtcaaaca gtattcttga atgttatacc ccagcccaaa ccatttcaac    2340
tgagtttgct gttaaattga aaattgactt agccaaccga gagacaagca tcttcagtta    2400
ccgtgaagat cccattgtct atgaaattca tccaaccaaa tcttttatta gtggtgggag    2460
cacaataaca ggtgttggga aaaacctgaa ttcagttagt gtcccgagaa tggtcataaa    2520
tgtgcatgaa gcaggaagga actttacagt ggcatgtcaa catcgctcta attcagagat    2580
aatctgttgt accactcctt ccctgcaaca gctgaatctg caactccccc tgaaaaccaa    2640 agccttttc atgttagatg ggatcctttc caaatacttt gatctcattt atgtacataa    2700
tcctgtgttt aagccttttg aaaagccagt gatgatctca atgggcaatg aaaatgtact    2760
ggaaattaag ggaaatgata ttgaccctga agcagttaaa ggtgaagtgt taaaagttgg    2820
aaataagagc tgtgagaata tacacttaca ttctgaagcc gttttatgca cggtccccaa    2880
tgacctgctg aaattgaaca gcgagctaaa tatagagtgg aagcaagcaa tttcttcaac    2940
cgtccttgga aaagtaatag ttcaaccaga tcagaatttc acaggattga ttgctggtgt    3000
tgtctcaata tcaacagcac tgttattact acttgggttt ttcctgtggc tgaaaaagag    3060
aaagcaaatt aaagatctgg gcagtgaatt agttcgctac gatgcaagag tacacactcc    3120
tcatttggat aggcttgtaa gtgcccgaag tgtaagccca actacagaaa tggtttcaaa    3180
tgaatctgta gactaccgag ctacttttcc agaagatcag tttcctaatt catctcagaa    3240
cggttcatgc cgacaagtgc agtatcctct gacagacatg tcccccatcc taactagtgg    3300
ggactctgat atatccagtc cattactgca aaatactgtc cacattgacc tcagtgctct    3360
aaatccagag ctggtccagg cagtgcagca tgtagtgatt gggcccagta gcctgattgt    3420
gcatttcaat gaagtcatag aagagggca ttttggttgt gtatatcatg gactttgtt    3480 ggacaatgat ggcaagaaaa ttcactgtgc tgtgaaatcc ttgaacagaa tcactgacat    3540
aggagaagtt tcccaatttc tgaccgaggg aatcatcatg aaagatttta gtcatcccaa    3600
tgtcctctcg ctcctgggaa tctgcctgcg aagtgaaggg tctccgctgg tggtcctacc    3660
atacatgaaa catggagatc ttcgaaattt cattcgaaat gagactcata atccaactgt    3720
aaaagatctt attggctttg gtcttcaagt agccaaaggc atgaaatatc ttgcaagcaa    3780
aaagtttgtc cacagagact ggctgcaag aaactgtatg ctggatgaaa aattcacagt    3840
caaggttgct gattttggtc ttgccagaga catgtatgat aaagaatact atagtgtaca    3900
caacaaaaca ggtgcaaagc tgccagtgaa gtggatggct ttggaaagtc tgcaaactca    3960
aaagtttacc accaagtcag atgtgtggtc ctttggcgtg ctcctctggg agctgatgac    4020
aagaggagcc ccaccttatc ctgacgtaaa cacctttgat ataactgttt acttgttgca    4080
agggagaaga ctcctacaac ccgaatactg cccagacccc ttatatgaag taatgctaaa    4140
atgctggcac cctaaagccg aaatgcgccc atcctttct gaactggtgt cccggatatc    4200
agcgatcttc tctactttca ttggggagca ctatgtccat gtgaacgcta cttatgtgaa    4260
cgtaaaatgt gtcgctccgt atccttctct gttgtcatca aagataacg ctgatgatga    4320 ggtggacaca cgaccagcct ccttctggga gacatcatag tgctagtact atgtcaaagc    4380
aacagtccac actttgtcca atggttttt cactgcctga cctttaaaag gccatcgata    4440
ttctttgctc ttgccaaaat tgcactatta taggacttgt attgttattt aaattactgg    4500
```

```
attctaagga atttcttatc tgacagagca tcagaaccag aggcttggtc ccacaggcca    4560
cggaccaatg gcctgcagcc gtgacaacac tcctgtcata ttggagtcca aaacttgaat    4620
tctgggttga attttttaaa aatcaggtac cacttgattt catatgggaa attgaagcag    4680
gaaatattga gggcttcttg atcacagaaa actcagaaga gatagtaatg ctcaggacag    4740
gagcggcagc cccagaacag gccactcatt tagaattcta gtgtttcaaa acacttttgt    4800
gtgttgtatg gtcaataaca ttttcatta ctgatggtgt cattcaccca ttaggtaaac    4860
attccctttt aaatgtttgt tgttttttg agacaggatc tcactctgtt gccagggctg    4920
tagtgcagtg gtgtgatcat agctcactgc aacctccacc tcccaggctc aagcctcccg    4980
aatagctggg actacaggcg cacaccacca tccccggcta ttttttgtat tttttgtaga    5040
gacggggttt tgccatgttg ccaaggctgg tttcaaactc ctggactcaa gaatccacc    5100 cacctcagcc tcccaaagtg ctaggattac aggcatgagc cactgcgccc agcccttata    5160 aattttgta tagacattcc tttggttgga agaatattta taggcaatac agtcaaagtt    5220
tcaaaatagc atcacacaaa acatgtttat aaatgaacag gatgtaatgt acatagatga    5280
cattaagaaa atttgtatga ataattag tcatcatgaa atatttagtt gtcatataaa    5340
aacccactgt ttgagaatga tgctactctg atctaatgaa tgtgaacatg tagatgtttt    5400
gtgtgtattt ttaaatga aaactcaaaa taagacaagt aatttgttga taaatatttt    5460
taaagataac tcagcatgtt tgtaaagcag gatacatttt actaaaaggt tcattggttc    5520
caatcacagc tcataggtag agcaaagaaa gggtggatgg attgaaaaga ttagcctctg    5580
tctcggtggc aggttcccac ctcgcaagca attggaaaca aaacttttgg ggagttttat    5640
tttgcattag ggtgtgtttt atgttaagca aaacatactt tagaaacaaa tgaaaaggc    5700 aattgaaaat cccagctatt tcacctagat ggaatagcca ccctgagcag aactttgtga    5760
tgcttcattc tgtggaattt tgtgcttgct actgtatagt gcatgtggtg taggttactc    5820
taactggttt tgtcgacgta aacatttaaa gtgttatatt ttttataaaa atgtttattt    5880
ttaatgatat gagaaaaatt tgttaggcc acaaaaacac tgcactgtga acatttttaga    5940 aaaggtatgt cagactggga ttaatgacag catgattttc aatgactgta aattgcgata    6000
aggaaatgta ctgattgcca atacacccca ccctcattac atcatcagga cttgaagcca    6060
agggttaacc cagcaagcta caaagagggt gtgtcacact gaaactcaat agttgagttt    6120
ggctgttgtt gcaggaaaat gattataact aaaagctctc tgatagtgca gagacttacc    6180
agaagacaca aggaattgta ctgaagagct attacaatcc aaatattgcc gtttcataaa    6240
tgtaataagt aatactaatt cacagagtat tgtaaatggt ggatgacaaa agaaaatctg    6300
ctctgtggaa agaaagaact gtctctacca gggtcaagag catgaacgca tcaatagaaa    6360
gaactcgggg aaacatccca tcaacaggac tacacacttg tatatacatt cttgagaaca    6420
ctgcaatgtg aaaatcacgt ttgctatta taaacttgtc cttagattaa tgtgtctgga    6480
cagattgtgg gagtaagtga ttcttctaag aattagatac ttgtcactgc ctatacctgc    6540
agctgaactg aatggtactt cgtatgttaa tagttgttct gataaatcat gcaattaaag    6600
taaagtgatg caacatcttg taaaaaaaaa aaaaaaaaa a                         6641
```

<210> SEQ ID NO 2
<211> LENGTH: 1378
<212> TYPE: PRT
<213> ORGANISM: Homo sapiens

<400> SEQUENCE: 2

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415
```

```
Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830
```

```
Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230
```

Tyr Tyr Ser Val His Asn Lys Thr Gly Ala Lys Leu Pro Val Lys
1235                1240                1245

Trp Met Ala Leu Glu Ser Leu Gln Thr Gln Lys Phe Thr Thr Lys
1250                1255                1260

Ser Asp Val Trp Ser Phe Gly Val Leu Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu
1370                1375

<210> SEQ ID NO 3
<211> LENGTH: 1048
<212> TYPE: DNA
<213> ORGANISM: Homo sapiens

<400> SEQUENCE: 3

```
aaggcggggg cggggcgggg gcggcggccg tgggtccctg ccggccggcg gcgggcgcag        60
acagcggcgg gcgcaggacg tgcactatgg ctcggggctc gctgcgccgg ttgctgcggc       120
tcctcgtgct ggggctctgg ctggcgttgc tgcgctccgt ggccggggag caagcgccag       180
gcaccgcccc ctgctcccgc ggcagctcct ggagcgcgga cctggacaag tgcatggact       240
gcgcgtcttg cagggcgcga ccgcacagcg acttctgcct gggctgcgct cagcaccctc       300
ctgcccccttt ccggctgctt tggcccatcc ttggggcgc tctgagcctg accttcgtgc       360
tggggctgct ttctggcttt ttggtctgga cgatgccg caggagagag aagttcacca       420
cccccataga gagaccggc ggagagggct gcccagctgt ggcgctgatc cagtgacaat       480
gtgcccctg ccagccgggg ctcgcccact catcattcat tcatccattc tagagccagt       540
ctctgcctcc cagacgcggc gggagccaag ctcctccaac cacaagggg gtggggggcg       600
gtgaatcacc tctgaggcct gggcccaggg ttcagggaa ccttccaagg tgtctggttg       660
ccctgcctct ggctccagaa cagaaaggga gcctcacgct ggctcacaca aaacagctga       720
cactgactaa ggaactgcag catttgcaca ggggagggg gtgccctcct tcctagaggc       780
cctggggcc aggctgactt ggggggcaga cttgacacta ggccccactc actcagatgt       840
cctgaaattc caccacgggg gtcaccctgg ggggttaggg acctattttt aacactaggg       900
ggctggccca ctaggagggc tggccctaag atacagaccc ccccaactcc ccaaagcggg       960
gaggagatat ttatttttggg gagagtttgg aggggaggga gaatttatta ataaaagaat     1020
ctttaacttt aaaaaaaaa aaaaaaaa                                           1048
```

<210> SEQ ID NO 4
<211> LENGTH: 129
<212> TYPE: PRT
<213> ORGANISM: Homo sapiens -continued

```
<400> SEQUENCE: 4

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln
```